United States Patent [19]

Barton et al.

[11] 4,370,497

[45] Jan. 25, 1983

[54] OXIDATION PROCESS USING TELLURIUM OXIDE CATALYSTS

[76] Inventors: Derek H. R. Barton, Centre Résidental du CNRS, 91190 Gif sur Yvette, France; Steven V. Ley, 10, Viney Bank, Addington, Surrey, United Kingdom, CR0 9JS; Clive A. Meerholz, 14 Southhall Close, Ware, Hertfordshire, United Kingdom, SG12 7PE

[21] Appl. No.: 175,847

[22] Filed: Aug. 7, 1980

[30] Foreign Application Priority Data

Aug. 8, 1979 [GB] United Kingdom ............... 7927604

[51] Int. Cl.³ .............................. C07C 127/19
[52] U.S. Cl. ............................ 564/55; 564/215; 564/217; 564/218; 564/224; 568/305; 568/306; 568/307; 568/308; 568/309; 568/383; 568/386; 568/408; 564/31; 564/123; 564/163; 564/168; 564/170; 564/177; 564/179; 564/182; 564/183; 564/184; 564/186; 564/187; 564/189; 564/190; 564/191; 564/193; 564/194; 564/197; 564/201; 564/202; 564/203; 564/204; 564/207; 564/208; 564/209; 564/210; 564/211; 564/214; 260/455 R; 260/455 B; 260/455 A; 260/463; 560/1; 560/24; 560/29; 560/30; 560/31; 560/32; 560/33; 560/43; 560/55; 560/58; 560/61; 560/115; 560/125; 560/126; 560/121; 560/123; 560/124; 560/131; 560/132; 560/136; 560/137; 560/142; 560/145; 560/157; 560/160; 560/162; 560/163; 560/165; 560/167; 560/179; 560/183; 560/185; 560/187; 560/188; 560/205; 560/219; 560/220; 560/221; 560/222; 560/223; 560/225; 560/226; 560/228; 560/229; 560/231; 560/250; 560/253; 560/254; 560/261

[58] Field of Search .............. 564/47, 55, 31, 123, 564/163, 168, 170, 177, 179, 182, 183, 184, 186, 187, 189, 190, 191, 193, 194, 197, 201, 202, 203, 204, 207, 208, 209, 210, 211, 214, 215, 217, 218, 224; 568/305, 306, 307, 308, 309, 383, 386, 408; 260/550, 687 R, 455 R, 455 B, 455 A, 463; 252/439; 560/1, 24, 29, 30, 31, 32, 33, 43, 55, 58, 61, 115, 125, 126, 121, 123, 124, 131, 132, 136, 137, 142, 145, 157, 160, 162, 163, 165, 167, 179, 183, 185, 187, 188, 205, 219, 220, 221, 222, 223, 225, 226, 228, 229, 231, 250, 253, 254, 261

[56] References Cited

U.S. PATENT DOCUMENTS 4,162,234  7/1979  Grasselli et al. ............... 252/439 X
4,238,624  12/1980  Morris et al. .................. 252/439 X

OTHER PUBLICATIONS

Richter, CA 47:10771ad (1954).
Suresh, CA 53:14030a (1959).
Lacey, CA 49:8944h (1955).

*Primary Examiner*—Thomas A. Waltz
*Attorney, Agent, or Firm*—Bacon & Thomas

[57] ABSTRACT

The present invention relates to the use of telluroxides as mild and selective oxidizing agents serving to oxidize certain functions, notably >C=S groups, in the presence of other relatively easily oxidized functions which remain unaffected; telluroxides of interest as oxidizing agents include, for example, compounds of the formula:

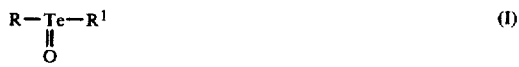

(I)

wherein R and R¹, which may be the same or different, each represent an optionally substituted aryl or heterocyclic group; or R and R¹ together with the tellurium atom therebetween represent a heterocyclic ring, which may contain one or more further heteroatoms, and which may carry substituents and/or fused aromatic rings.

8 Claims, No Drawings

OXIDATION PROCESS USING TELLURIUM OXIDE CATALYSTS

The present invention relates to the use of telluroxides as oxidizing agents and to oxidation reactions in which telluroxides are used as oxidising agents.

The present invention is based on the discovery that telluroxides may be used as mild and selective oxidising agents serving to oxidise certain functions, notably >C=S groups, in the presence of other relatively easily oxidised functions which remain unaffected.

Telluroxides of interest as oxidising agents include, for example, compounds of the formula:

(I)

wherein R and $R^1$, which may be the same or different, each represent an optionally substituted aryl or heterocyclic group; or R and $R^1$ together with the tellurium atom therebetween represent a heterocyclic ring, which may contain one or more further heteroatoms, and which may carry substituents and/or fused aromatic rings, for example one of the groups

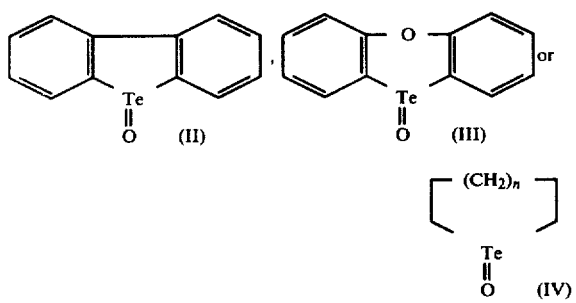

in which n is 0 or 1, which groups may be optionally substituted.

Where R and/or $R_1$ represents an aryl or heterocyclic group such groups may, for example, be phenyl, 1-naphthyl, 2-naphthyl, 2-thienyl, 9-anthryl, 1-pyrenyl or biphenyl.

Substituents which may be present particularly on aromatic rings, include, for example, halogen (e.g. fluorine, chlorine or bromine), alkyl, phenyl, phenoxy, alkoxy, dialkylamino, hydroxy, carboxy, reactive ester e.g. chlorocarbonyl or nitro. Where an alkyl group or moiety is present such groups or moieties are conveniently lower alkyl having for example 1 to 6, preferably 1 or 2, carbon atoms. Alkoxy groups may, for example, carry further substituents such as esterified carboxyl groups, e.g. alkoxy-carbonyl groups. Where an aryl moiety is bonded directly to the tellurium atom it is advantageously substituted, preferably in the o and/or p-position, by at least one electron donating substituent, for example an alkoxy, e.g. methoxy, group or a dialkylamino e.g. dimethylamino group.

R and $R_1$ in the compounds of formula I may carry one or several substituents. Thus for example where R and/or $R_1$ represents a phenyl group each phenyl group may carry from 1 to 5 substituents for example 2-methyl, 3-methyl, 4-methyl, 4-phenyl, 2,4-dimethyl, 2,5-dimethyl, 2,4,6-trimethyl, 2-methoxy, 3-methoxy, 4-methoxy, 2-ethoxy, 4-ethoxy, 4-bromo, 4-chloro, 2-carboxy, 4-dimethylamino, 4-hydroxy, 4-fluoro, 3-chloro, 4-nitro, 3-methyl-4-methoxy, 2,4-dimethoxy, 3,4-dimethoxy or 2,3,4,5,6-pentafluoro substituents.

The telluroxides for use as oxidising agents may be either symmetrical or asymmetrical. Thus for example R and $R_1$ in asymmetric compounds of formula I may respectively represent phenyl and 2-methylphenyl, phenyl and 4-methylphenyl, phenyl and 4-methoxyphenyl, phenyl and 4-ethoxyphenyl, phenyl and 4-phenoxyphenyl, phenyl and 3-fluorophenyl, phenyl and 4-bromophenyl, phenyl and 4-dimethylaminophenyl, phenyl and 4-chlorophenyl, 4-bromophenyl and 4-dimethyl-aminophenyl, 4-methoxyphenyl and 4-dimethylaminophenyl, 4-ethoxyphenyl and 4-dimethylaminophenyl, 4-phenoxyphenyl and 4-dimethylaminophenyl, 4-methoxyphenyl and 4-ethoxyphenyl, 1-naphthyl and phenyl, 2-napthyl and phenyl, 1-napthyl and 4-methoxyphenyl, 2-napthyl and 4-methoxyphenyl, 1-naphthyl and 4-ethoxyphenyl, 1-naphthyl and 4-phenoxy-phenyl, 2-naphthyl and 4-phenoxyphenyl, 1-naphthyl and 2-naphthyl, 1-chlorocarbonylphenyl and phenyl and 1-chloro-carbonylphenyl and 2,4,6-trimethylphenyl.

Similar substituents may be present on the ring structures of formulae (II), (III) and (IV). Thus, in particular, the telluroxide may have the formula:

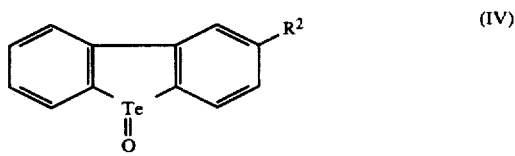

in which $R^2$ represents a hydrogen atom or a methyl group or preferably an electron donating substituent such as an alkoxy, e.g. methoxy, group or a dialkylamino, e.g. dimethylamino, group.

Telluroxides may be used, as indicated above, as mild and highly selective oxidising agents. The following reactions are particularly valuable:

(1) telluroxides may be used to convert a >C=S or >C=Se group to a >C=O group. Thus, for example compounds of the formula:

$R^3(X^1)_m.CO.(X^2)_nR^4$  VI (wherein $X^1$ and $X^2$ which may be the same or different each represents a sulphur, oxygen or nitrogen atom, m and n, which may be the same or different, are each 0 or 1 and $R^3$ and $R^4$, which may be the same or different, each represent hydrocarbyl groups e.g. optionally substituted aliphatic, cycloaliphatic, araliphatic or aromatic groups such as $C_{1-5}$ alkyl or alkenyl groups, $C_{1-32}$ cycloalkyl groups optionally including double bonds, $C_{7-10}$ aralkyl groups or $C_{6-12}$ e.g. $C_{6-10}$ aryl groups such groups optionally carrying substituents such as halogen amino, carboxyl, hydroxy, $C_{1-6}$ alkyl or $C_{1-6}$ alkoxy groups or $R^3$ and $R^4$ together form a ring(s) which may possess up to 32 carbon atoms and which may have double bonds and be optionally substituted as hereinbefore described) may be prepared by reaction of a compound of the formula:

$R^3(X^1)_m.CS.(X^2)_nR^4$  VII (wherein $R^3, R^4, X^1, X^2$, m and n are as herein defined) or the corresponding seleno compound with a telluroxide for example of formula I as hereinbefore defined.

The >C=S or >C=Se group in the compound of formula VII may thus be, for example, part of a xanthate, thiocarbonate, thiourea, thioester or thione or a corresponding seleno compound e.g. a selenocarboxylate such as a selenobenzoate.

Thus, for example, the compound of formula VII may be 5-cholesten-3β-ol-thionoacetate, 5-cholesten-3β-ol-thiono-benzoate, 5α-cholestan-3β-ol-xanthate, 5α-cholestan-3β-ol-selenobenzoate, thiofenchone, di-tert.-butyl thioketone, thiocamphor, phenylisothiocyanate, cyclohexan-1,2-trans-diyl-dithio-thiocarbonate, thiourea and 1,3-diphenylthiourea.

In particular thiocarbamates of the general formula: $R^3$—O—CS—$NR^4$ may be oxidised to carbamates of the formula $R^3$—O—CO—$NR^4$. Such carbamates are of particular interest in agrochemistry as pesticides, fungicides and herbicides but their conventional synthesis involves the use of phosgene which is hazardous for use on an industrial scale. However thiocarbamates can be synthesised using carbon disulphide and subsequent facile oxidation by a telluroxide yields a particularly attractive preparative method for producing carbamates.

(2) Thiols of the formula $R^3SH$ wherein $R^3$ is as hereinbefore defined, including thiol containing amino acids and enethiols may be converted into their corresponding disulphides by reaction of the thiol with a telluroxide e.g. of formula I as hereinbefore defined.

Telluroxides may for example be used to convert cysteine to cystine by the formation of a disulphide bond, whereas some other oxidising agents are too vigorous to effect this conversion.

(3) Catechols and hydroquinones may be converted into the corresponding o-and p-quinones.

(4) Telluroxides may also be used to oxidise arylhydrazines to the corresponding hydrocarbon with evolution of nitrogen. Where an aryl telluroxide, having an aryl moiety different from that of the hydrazine, is used, however, aryl exchange may also take place to form an asymmetrical telluride. Moreover where electron withdrawing groups are present in the aryl moiety as, for example, in 4-nitrophenylhydrazine and 2,4-dinitrophenylhydrazine, complex reaction mixtures tend to be formed.

(5) Isothiocyanates may be converted to ureas and thus phenyl isothiocyanate, on oxidation with a telluroxide in the presence of water (e.g. of formula (I) as hereinbefore defined), gives 1,3-diphenylurea.

(6) Hydrazones may be converted to corresponding diazo compounds. Thus benzophenone yields diphenyldiazomethane; if an acid, for example, anisic acid, is added after the reaction, a diphenylmethyl ester can be recovered.

(7) Arylhydroxylamines may be converted to nitrosoarenes. Thus for example phenylhydroxylamine may be oxidised in good yield to nitrosobenzene. Indeed we have been able to obtain nitrosobenzene in 90% yield from phenylhydroxylamine using bis-(p-methoxyphenyl)-telluroxide.

Telluroxides are of particular interest as oxidising agents, however, because they may be used to oxidise certain functions selectively in the presence of other functions which are relatively easily oxidised. Thus, for example, no reaction has been found with relatively easily oxidised substrates such as phenols; alcohols; enamines; amines for example pyrrole, indole, tryptophan, tyrosine, aniline and N,N-dimethylaniline; oximes; dithiolanes, isonitriles and 2,4-dinitrophenylhydrazones.

The oxidation is advantageously effected at a temperature of from 0° to 60° C. preferably about ambient temperature. Solvents for the oxidation reaction include halogenated, for example chlorinated, hydrocarbons preferably chloroform or dichloromethane. Preferably at least one equivalent of telluroxide is used per equivalent of the substance to be oxidised, unless the telluroxide is used catalytically, as explained in detail hereinafter.

A number of telluroxides including the compounds of the formula

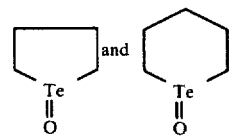

are described in K. J. Irgolic, "The Organic Chemistry of Tellurium", Gordon and Breach, New York, 1974, 194., and processes for their preparation are set out in the references cited therein.

Telluroxides may be prepared according to any convenient method described in the literature or by analogous methods. Thus for example symmetric or asymmetric aryl telluroxides may be prepared by aqueous hydrolysis of a diaryl tellurium dihalide in the presence of a base such as triethylamine, or for example sodium or potassium hydroxide. The hydrolysis is generally effected at an elevated temperature, for example 90° to 100° C.

The diaryl tellurium dihalide may be prepared in any convenient manner including:

(a) reaction of a tellurium tetrahalide with an arene at an elevated temperature in an inert atmosphere e.g. under nitrogen;

(b) reaction of a symmetrical or asymmetrical diaryl telluride with a halogenating agent, such as a sulphonyl halide; for the preparation of asymmetrical diaryl tellurides a symmetrical diaryl telluroxide may be reacted, as mentioned above, with an aryl hydrazine, the aryl moiety of the telluroxide being different from the aryl moiety of the hydrazine.

The telluroxide reagent may advantageously be prepared in situ by reaction of the corresponding telluride in the presence of water and a base, using a halogenating agent therefore which is sufficiently stable under the reaction conditions to effect the desired selective reaction. Suitable halogenating agents include chlorine and bromine, and especially vicinal dibromides such as vicinal dibromoalkanes and vicinal dibromoaralkanes which may carry substituents, for example halogen, such as chlorine or carboxy, and which may be acyclic e.g. 1,2-dibromoethane, 1,2-dibromo-1,2-diphenylethane, 1,2-dibromo-2-phenyl propionic acid (1,2-dibromohydrocinnamic acid) or vicinal dibromoperhaloalkanes e.g. symmetrical dibromotetrachloroethane; or cyclic e.g. 1,2-dibromocyclohexane, 1,2-dibromocholesterol or 5β, 6β-dibromocholestane. Allylic bromides e.g. allyl bromide may also be used. High valency transition metal halides for example mercuric chloride but especially ferric or cupric chloride may be used as the halogenating agent, the halogenation conveniently being effected at an elevated temperature, for example in the presence of acetic acid or xylene.

Since the oxidation of the substrate reduces the telluroxide to the telluride, an excess of halogenating agent in the presence of the aqueous base will continually regenerate the telluroxide and thus only a catalytic quantity of the telluroxide is required, the oxidation being primarily effected by the halogenating agent.

Thus the catalytic oxidation reaction may be depicted:

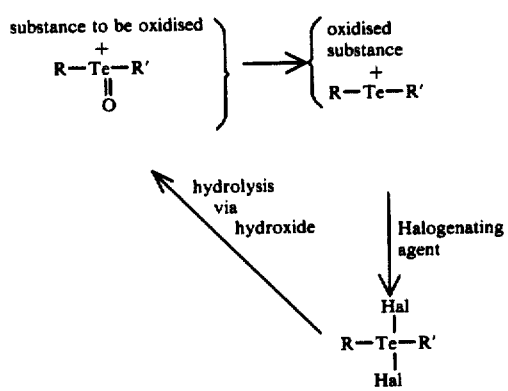

Since telluride, dihalotelluride and telluroxide all feature in the catalytic process, any of these can be added initially to the reaction mixture as the catalyst. The most preferred halogenating agent for use in the catalytic reaction is symmetrical dibromotetrachloroethane due to its inertness to a wide range of oxidisable substrates. The overall reaction proceeds under mild conditions, the reaction temperature being conveniently in the range 0°–60° C., usually at about room temperature. A solvent for the substrate should be present, for example a chlorinated aliphatic hydrocarbon such as chloroform or dichloromethane, which may form a two phase system with the water component, although where the substrate and the halogenating agent are water soluble, water may be the sole solvent present.

The tellurium-containing reactant in the catalytic reaction is preferably present in quantities in the range 0.01 to 0.1 moles based on the substrate. The halogenating agent, e.g. symmetrical dibromotetrachloroethane, is preferably present in excess, for example in the range 3 to 10 moles based on the substrate. The water is preferably present in considerable excess, for example, in approximately equal quantities to those of the reaction solvent. In general, the substrate is preferably in dilute solution, e.g. in the range 0.5% to 10% by weight.

The base used in the reaction may be organic, for example a tertiary organic amine e.g. triethylamine, or inorganic, for example an alkali metal carbonate or hydroxide e.g. potassium or sodium carbonate. In general, the quantity of base used will be in the range 5 to 40 moles based on the substrate.

The following preparations illustrate the production of telluroxides for use in oxidation reactions according to the present invention:

Preparations:

PREPARATION 1

Bis-(p-methoxyphenyl)telluroxide

Tellurium tetrachloride (7.50 g, 28 mmol) and anisole (15 g, 139 mmol) were stirred at 180° for 18 h under a slow stream of nitrogen. After this time 48 mmol of hydrogen chloride had been evolved and the excess anisole was removed under high vacuum. The remaining brown solid was recrystallised from benzene to afford bis-(p-methoxyphenyl)tellurium dichloride (10.05 g, 88%), m.p. 181°–182° (lit., 181°–182°), $\delta(CDCl_3)$ 8.01 (4H,d,J 9 Hz), 7.03 (4H,d,J 9 Hz) and 3.89 (6H,s).

The bis-(p-methoxyphenyl)tellurium dichloride (8.00 g, 19.4 mmol) was stirred at 95° in aqueous sodium hydroxide (100 ml, 5%) for 1 h. After cooling in an ice bath the white solid was filtered and dried under vacuum over phosphorus pentoxide to give bis-(p-methoxyphenyl)telluroxide (5.60 g, 81%), m.p. 187°–189° (lit., 190°–191°) vmax (Nujol) 1585,1575,1490,1460,1401,1380,1295,1247,1180,1172,1109,1068,1026,823,811 and 789 cm$^{-1}$.

PREPARATION 2

4-Methoxy-4'-dimethylaminodiphenyltelluroxide

4-Methoxy-4'-dimethylaminodiphenyltellurium dichloride (1.223 g, 2.878 mmol) [prepared as described in N. Petragnani, Tetrahedron, 1961, 12,219] was stirred at 80° for 0.75 h in aqueous sodium hydroxide (20 ml, 5%). After cooling in an ice bath the white precipitate was filtered, washed with water (3×5 ml) and dried under vacuum over phosphorus pentoxide to give 4-methoxy-4'-dimethylaminodiphenyltelluroxide (0.886 g, 84%) m.p. 209°–210.5° $\delta(CDCl_3)$7.62 and 7.52 (combined integral 4H, both d, J 9 Hz), 6.92 and 6.67 (combined integral 4H, both d, J 9 Hz), 3.79 (3H,s), and 2.97 (6H,s).

PREPARATION 3

Diphenyltelluroxide

Diphenyltelluroxide was prepared from diphenyltellurium dichloride by the aqueous base hydrolysis procedure described in H. Rheinboldt and E. Giesbrecht, J. Amer. Chem. Soc., 1947, 69, 2310.

PREPARATION 4

Bis-(p-methoxycarbonylmethoxyphenyl)telluroxide

Tellurium tetrachloride (11.36 g, 0.042 mol) and methyl phenoxy acetate (21.00 g, 0.127 mol) were refluxed in carbon tetrachloride (175 ml) for 18 h. The reaction solution was filtered while still hot, the filtrate cooled in an ice bath and the resulting solid filtered to afford p-methoxycarbonylmethoxyphenyltellurium trichloride (16.11 g, 96%) $\delta(CDCl_3/DMSO\ d^6)$ 8.38 (2H,d,9Hz), 6.90 (2H,d,9 Hz), 4.67 (2H,s), and 3.77 (3H,s). No attempt was made to purify this compound and it was used directly in the next step.

The trichloride (16.00 g, 0.040 mmol) and potassium metabisulphite (27.00 g, 0.121 mmol) were stirred in a two phase system of dichloromethane (200 ml) and water (200 ml) for 1 h at room temperature. The two phases were separated, the aqueous phase extracted with dichloromethane (3×30 ml) and the combined organic phases dried over magnesium sulphate. Filtration and evaporation of the filtrate under reduced pressure gave a red-brown oil which solidified on standing to afford bis-(p-methoxycarbonylmethoxyphenyl)-ditelluride (11.10 g, 95%) m.p. 68°–74° (decomposition), $\delta(CDCl_3)$ 7.62 (4H,d,9 Hz), 6.70 (4H,d,9 Hz), 4.60 (4H,s), and 3.78 (6H,s), m/e 590 (M+), 460,330,257,166, and 79 (100%).

The ditelluride (1.900 g, 0.325 mmol) and activated copper powder (0.618 g, 0.974 mmol) were refluxed under nitrogen in dry dioxan (50 ml) for 2 h. Filtration and evaporation of the dioxan under reduced pressure gave a cream solid which after column chromatography (benzene-ethyl acetate 9:1) afforded bis-(p-methoxycarbonylmethoxyphenyl)telluride (1.46 g) 98%). Recrystallisation from methanol gave fine white needles m.p. 108°–109°, $\nu$ max (CHCl$_3$) 2900,1760,1590,1485,1440,1375,1295,1175,1090, and 1010 cm$^{-1}$. $\delta$(CDCl$_3$) 7.62 (4H,d,J9 Hz), 6.73 (4H,d,J9 Hz), 4.60 (4H,s), and 3.80 (6H,s), m/e 460(M$^+$), 330,293,258, and 257 (100%) (Found: C,47.24;H,3.90 Calc. for C$_{18}$H$_{18}$O$_6$Te: C, 47.21; H,3.96%).

The telluride (2.670 g, 5.835 mmol) was dissolved in benzene (80 ml) and treated with sulphuryl chloride (0.52 ml, 6.419 mmol). After 0.5 h. the benzene was removed under reduced pressure to afford a sticky white solid which is thought to be bis-(p-methoxycarbonylmethoxyphenyl)-tellurium dichloride (3.080 g, 100%), $\nu$ max (Film) 3090,3070,3010,2955,2925,2855,1756,1584,1575,1490,14-38,1402,1376,1311,1300,1215,1180,1124,1076,1000,822, and 755 cm$^{-1}$.

$\delta$(CDCl$_3$) 7.97 (4H,d,9 Hz), 6.98 (4H,d,9Hz), 4.65 (4H,s), and 3.80 (6H,s).

The tellurium dichloride (752 mg, 1.423 mmol) was dissolved in dichloromethane (5 ml) and shaken with aqueous potassium carbonate (6 ml, 5%) for 0.3 h. The phases were separated, the aqueous phase extracted with dichloromethane (2×10 ml) and the combined dichloromethane extracts dried over magnesium sulphate. Filtration and evaporation of the filtrate gave a frothy white solid which is thought to be the bis-(p-methoxycarbonylmethoxyphenyl)telluroxide (644 mg 95%), $\delta$(CDCl$_3$) 7.52 (4H,d,J 8 Hz), 6.72 (4H,d,J 8 Hz), 4.59 (4H,s), and 3.77 (6H,s).

The following Examples illustrate processes according to the present invention:

In the following Examples 1–12 the reactions were effected at room temperature under nitrogen (balloon) in either chloroform or dichloromethane. Approximately 10 ml of solvent was used for every 100 mg of thiocarbonyl compound; 1.1 equivalents of bis-(p-methoxyphenyl)-telluroxide were employed. The reaction mixtures were concentrated by partial evaporation of the solvent and subjected to preparative layer chromatography (p.l.c.) (silica) or column chromatography (c.c.) (silica) to isolate the products. The product yields refer to the chromatographic yields unless otherwise specified. Bis-(p-methoxyphenyl)telluride was always recovered in yields ranging from 64 to 96%. The physical and spectroscopic data for this compound are as follows; m.p. 50–51.5 (lit., 53°–54°), $\delta$(CDCl$_3$) 7.58 (4H,d,J 8 Hz), 6.70 (4H,d,J 8 Hz) and 3.75 (6H s), m/e 344 M$^{(+)}$, 214 (100%), 199), and 152. Sulphur or selenium were always recovered in near quantitative yields. The product yields together with the reaction times and physical and spectroscopic data are presented below.

EXAMPLE 1

Oxidation of 5-Cholesten-3$\beta$-ol-thionoacetate

5-Cholesten-3$\beta$-ol-thionoacetate (111 mg, 0.25 mmol), was reacted with bis-(p-methoxyphenyl)-telluroxide for 0.25 h. 5-Cholesten-3$\beta$-ol-acetate (107 mg, 100%) was obtained after P.l.c. (petroleum ether-ethyl acetate 9:1. The product obtained was recrystallized from acetone (90 mg, 84%), m.p. 113°–114° (lit., 114°–115°).

EXAMPLE 2

Oxidation of 5-Cholesten-3$\beta$-ol-dithionobenzoate

5-Cholesten-3$\beta$-ol-dithionobenzoate (130 mg, 0.25 mmol) was reacted with bis-(p-methoxyphenyl)-telluroxide for 27 h. 5-Cholesten-3$\beta$-thiol-benzoate (88 mg, 70%), m.p. 160°–162° was obtained after p.l.c. (petroleum ether-ethyl acetate 20:1). The product obtained was recrystallised from ethyl acetate (65 mg, 52%), m.p. 164.5–166 (lit., 167°), $\nu$max. (CCl$_4$) 2800,2750,1670,1550,1250,1210,1180,920,865,810–740 (broad) and 700 cm$^{-1}$, m/e 506 (M$^+$ weak), 369, and 368 (100%).

EXAMPLE 3

Oxidation of 5-Cholesten-3$\beta$-ol-thionobenzoate

5-Cholesten-3$\beta$-ol-thionobenzoate (253 mg, 0.50 mmol) was reacted with bis-(p-methoxyphenyl)-telluroxide for 1.5 h. 5-Cholesten-3$\beta$-ol-benzoate (162 mg, 66%) m.p. 143°–145° was obtained after p.l.c. (petroleum ether-ethyl acetate 9:1). The product obtained was recrystallized from ethyl acetate (130 mg, 53%), m.p. 144.5 (lit., 150°–151°), $\nu$max (CCl$_4$) 1722 cm$^{-1}$.

EXAMPLE 4

Oxidation of 5$\alpha$-Cholestan-3$\beta$-ol-xanthate

5$\alpha$-Cholestan-3$\beta$-ol-xanthate(116 mg, 0.25 mmol) was reacted with bis-(p-methoxyphenyl)-telluroxide for 24 h. 5$\alpha$-Cholestanyl-3$\beta$-ol-methylthiocarbonate (114 mg, 100%) m.p. 117°–119° were obtained after p.l.c. (petroleum ether-ethyl acetate 9:1). The product obtained was recrystallized from ethyl acetate (80 mg, 72%) m.p. 119.5–120.5 (lit., 117°), $\nu$max (CHCl$_3$) 1700 cm$^{-1}$, m/e 462 (M$^+$ weak), 371,355,258,256 (100%), 192,160, and 128.

EXAMPLE 5

Oxidation of 5$\alpha$-Cholestan-3$\beta$-ol-selenobenzoate

5$\alpha$-Cholestan-3$\beta$-ol-selenobenzoate (278 mg, 0.50 mmol) was reacted with bis-(p-methoxyphenyl)-telluroxide for 0.3 h. 5$\alpha$-Cholestan-3$\beta$-ol-benzoate (229 mg, 93%) was obtained after p.l.c. (petroleum ether-ethyl acetate 9:1). The product obtained was recrystallized from ethyl acetate (198 mg, 80%) m.p. 136°–137° (lit., 136°–137°).

EXAMPLE 6

Oxidation of Thiofenchone

Thiofenchone (23 mg, 0.14 mmol) was reacted with bis-(p-methoxyphenyl)telluroxide for 42 h. Fenchone (5 mg, 23%) $\nu$max 1965,1930,1875,1742,1465,1385 and 1025 cm$^{-1}$ was obtained after p.l.c. (petroleum ether-ethyl acetate 20:1). A low yield was obtained due to volatility of the product. Sulphur and bis-(p-methoxyphenyl)telluride were, however, isolated in 75 and 81% yields respectively.

EXAMPLE 7

Oxidation of Di-tert.-butylthioketone

Di-tert.-butylthioketone (197 mg, 1.25 mmol) was reacted with bis-(p-methoxyphenyl)telluroxide for 0.3 h. G.l.c shows quantitative conversion into di-t-butylketone, $\nu$max (crude reaction mixture) 1680 cm$^{-1}$. P.l.c.

EXAMPLE 8

Oxidation of Thiocamphor

Thiocamphor (168 mg, 1 mmol) was reacted with bis-p-methoxyphenyl)telluroxide for 2 h. to give a mixture of bis-(p-methoxyphenyl)-telluride and camphor (10% by g.l.c.) plus a non-polar product, which appears to be a diastereomeric mixture of bis-vinyldisulphide derivatives of thiocamphor (116 mg, 70%) which slowly convert on standing via a hetero Cope reaction to the dithione m.p. 174°–177° (lit., 173°–174° for optically pure sample), δ(CDCl$_3$) 2.50 (s), 2.33 (distorted doublet) integral ratio 1:1 and 2.2–0.6 (m). P.l.c. (petroleum ether followed by petroleum ether-ethyl acetate 9:1). No sulphur could be isolated in this reaction.

EXAMPLE 9

Oxidation of Phenylisothiocyanate

Phenylisothiocyanate (121 mg, 0.90 mmol) was reacted with bis-(p-methoxyphenyl)telluroxide for 0.25 h, [c.c. (ethylacetate)] to afford 1,3-diphenylurea (50 mg, 52%) after hydrolysis, m.p. 236°–238° (lit., 238°–239°), m/e 212 (M+), 119,93 (100%), 77,66, and 65.

EXAMPLE 10

Oxidation of Cyclohex-1,2-trans-diyl-dithio-thiocarbonate.

Trithiocarbonate (95 mg, 0.5 mmol) was reacted with bis-(p-methoxyphenyl)-telluroxide for 20 h [c.c. (petroleum ether followed by petroleum ether-ether 9:1)] to afford sulphur (16 mg, 100%) and a mixture of bis-(p-methoxyphenyl)-telluride and cyclohexan-1,2-trans-diyl-dithiocarbonate (228 mg) νmax (CHCl$_3$ mixture) 1730 and 1640 cm$^{-1}$, δ(CDCl$_3$ mixture) 7.58 (4H,d,J 8 Hz), 6.70 (4H,d,J 8 Hz), 3.75 (8H, overlapping s and m), and 2,30–1,25 (8H,m).

EXAMPLE 11

Oxidation of Thiourea (a) Thiourea (38 mg, 0,5 mmol) was reacted with bis-(p-methoxyphenyl)-telluroxide for 16 h. (methanol as solvent) to afford urea (22 mg, 73%), νmax (Nujol) 1660 broad cm$^{-1}$, p.l.c. (benzene followed by ethyl acetate).

(b) Thiourea (38 mg, 0.5 mmol) was reacted with bis-(p-methoxyphenyl)-telluroxide for 63 h (water as solvent), extraction of aqueous phase with dichloromethane and evaporation of water under vacuum afforded urea (34 mg, 100%).

EXAMPLE 12

Oxidation of 1,3-Diphenylthiourea 1,3-Diphenylthiourea (114 mg, 0,5 mmol) was reacted with bis-(p-methoxyphenyl)-telluroxide for 16 h (methanol as solvent), the methanol was evaporated off under vacuum, the residue triturated with benzene and filtered to afford 1,3-diphenylurea as a white solid (72 mg, 68%), m.p. 234° (lit., 238°–239°).

EXAMPLE 13

Oxidation of 5-Cholesten-3β-ol-thionobenzoate via a Catalytic Process

The thionobenzoate (200 mg, 0.40 mmol), bis-(p-methoxyphenyl)-telluride (2 mg, 0.006 mmol) and sym-tetrachloro dibromoethane (654 mg, 2 mmol) were vigorously stirred in a two phase system of chloroform (2 ml) and aqueous potassium carbonate (5 ml, 20%) for 20 h. The two phases were separated, the aqueous phase extracted with chloroform (2×5 ml) and the combined organic phases dried over magnesium sulphate. Evaporation of the chloroform under reduced pressure and purification of the residue by column chromatography (petroleum ether to elute the unreacted sym-tetrachloro-dibromoethane and then petroleum ether-ethyl acetate 20:1) afforded 5-cholesten-3-β-ol-benzoate (141 mg, 72%), m.p. 143°–145° (lit., 150°–151° ), ν max (CHCl$_3$)2945,2910,2870,1712,1602,1585,1275, and 1118 cm$^{-1}$.

EXAMPLE 14

Oxidation of 5-Cholesten-3β-ol-dithionobenzoate via a Catalytic Process

The dithionobenzoate (209 mg, 0,4 mmol), bis-(p-methoxyphenyl)-telluride (2 mg, 0.006 mmol) and sym-tetrachlorodibromoethane (1.288 g, 4 mmol) were vigorously stirred in a two phase system of chloroform (2 ml) and aqueous potassium carbonate (5 ml, 20%) for 72 h. Examination of the reaction by t.l.c. (petroleum ether followed by petroleum ether-benzene 8:2) showed complete reaction.

EXAMPLE 15

Oxidation of Di-tert.-butylthioketone

The thioketone (63 mg, 0.40 mmol), bis-(p-methoxyphenyl)-telluride (2 mg, 0.006 mmol) and sym-tetrachlorodibromoethane (644 mg, 2 mmol) were stirred in a two phase system of chloroform (2 ml) and aqueous potassium carbonate (5 ml, 20%). After 15 h the colour of the di-tert.-butyl-thioketone had been completely discharged.

Example 16

Oxidation of Cyclohexan-1,2-trans-diyl-dithio-thiocarbonate

The trithiocarbonate (76 mg, 0.40 mmol), bis-(p-methoxyphenyl)-telluride (2 mg, 0.006 mmol) and sym-tetrachlorodibromoethane (644 mg, 2 mmol) were stirred in a two phase system of chloroform (2 ml) and aqueous potassium carbonate (5 ml, 20%). After 72 h t.l.c. (petroleum ether followed by petroleum ether-benzene 1:1) showed complete reaction.

EXAMPLE 17

Oxidation of p-Thiocresol p-Thiocresol (246 mg, 1.98 mmol) and bis-(p-methoxyphenyl)-telluroxide (358 mg, 1 mmol) were stirred in chloroform (3 ml) at room temperature under a nitrogen atmosphere. After 0.1 h the reaction mixture was concentrated by partial evaporation of the solvent and subjected to p.l.c. (petroleum ether-ethyl acetate 9:1) to afford bis-(p-methoxyphenyl)-telluride (27° mg, 76%) and di-p-tolyldisulphide (239 mg, 98%) m.p. 44°–45°. The latter was recrystallised from ethanol to give the disulphide (202 mg, 83%) m.p. 47°–47.5° (lit., 48°)

δ(CDCl$_3$) 7.37 (4H,d,J 8 Hz), 7.05 (4H,d,J 8 Hz), and 2.30 (6H,s).

EXAMPLE 18

Oxidation of Thiobenzyl Alcohol

Thiobenzyl alcohol (0.10 ml, 0.85 mmol) and bis-(p-methoxyphenyl)-telluroxide (153 mg, 0.42 mmol) were stirred in chloroform (10 ml) at room temperature under a nitrogen atmosphere. After 0.5 h the reaction mixture was concentrated by partial evaporation of the solvent and subjected to p.l.c. (petroleum ether and then petroleum ether-ethyl acetate acetate 19:1) to afford bis-(p-methoxyphenyl)-telluride (84 mg, 58% and dibenzyldisulphide (100 mg. 96%). The latter was recrystallised from ethanol to give the disulphide (80 mg, 77%) m.p. 68.5°–70° (lit., 71°–72° and 69°–70°), δ(CDCl$_3$)7.27 (10H,s) and 3.57 (4H,s).

EXAMPLE 19

Oxidation of L-Cysteine Hydrochloride

L-Cysteine hydrochloride (157 mg, 1 mmol), bis-(p-methoxyphenyl)-telluroxide (197 mg, 0.55 mmol) and sodium acetate (82 mg, 1 mmol) were stirred at room temperature under nitrogen in de-oxygenated water (7 ml) for 1.5 h. The heterogeneous reaction mixture was then filtered, the insoluble white solid washed with water (2×2 ml), ethanol (2×2 ml) and finally chloroform (4×2 ml) to afford L-cystine (95 mg, 79%), m.p. 260° decomposition (lit., 258°–261° decomposition), νmax (KBr) 2900 broad, 2030, 1620 shoulder, 1580 broad, 1470, 1400, 1380, 1335, 1295, 1190, 1120, 1085, 1035, 960, 875, 850, 780, and 680. The filtrate was evaporated under reduced pressure and column chromatography (petroleum ether-ethyl acetate 9:1) of the residue afforded bis-(p-methoxydiphenyl)-telluride (121 mg, 68%).

EXAMPLE 20

Oxidation of p-Aminothiophenol p-Aminothiophenol (200 mg, 1.60 mmol) and bis-(p-methoxyphenyl)-telluroxide (300 mg, 084 mmol) were stirred in chloroform (3 ml) at room temperature under nitrogen for 1 h. Evaporation of the solvent under reduced pressure and column chromatography (benzene-ethyl acetate 8:2) of the residue afforded bis-(p-methoxyphenyl)telluride (246 mg, 85%) and 4,4'-diaminodiphenyl disulphide (114 mg, 58%) m.p. 73.5°–75° (lit., 85° and 106°), δ(CDCl$_3$)7.77 (4H,d,J 8 Hz), 6.57 (4H,d,J 8 Hz), and 3.67 (4H, s broad).

EXAMPLE 21

Oxidation of 2,4-Di-tert.-butylcatechol 2,4-Di-tert.-butylcatechol (111 mg, 0.50 mmol) and bis-(p-methoxyphenyl)-telluroxide (358 mg, 1 mmol) were stirred in chloroform (4 ml) at room temperature under N$_2$ for 24 h. The reaction mixture was concentrated by evaporation of the solvent under reduced pressure and after p.l.c. (petroleum ether-ethyl acetate 9:1) gave 2,4-di-tert.-butyl-o-benzoquinone (88 mg, 80%) as a deep red, crystalline solid m.p. 112°–114° (lit., 113°–114°), δ(CDCl$_3$) 6.92 (1H, d, J 2 Hz), 6.18 (1H, d, J 2 Hz), 1.29 and 1.23 (both s, combined integral 18H), No bis-(p-methoxyphenyl)-telluride was isolated.

EXAMPLE 22

Oxidation of 1,4-Dihydroxynaphthalene 1,4-Dihydroxynaphthalene (80 mg, 0.50 mmol) and bis-(p-methoxyphenyl)-telluroxide (196 mg, 0.55 mmol) were stirred in chloroform (4 ml) at room temperature under argon for 1 h. The reaction mixture was concentrated by evaporation of the solvent under reduced pressure and p.l.c. (benzene-ethyl acetate 9:1) gave bis-(p-methoxyphenyl)-telluride (96 mg, 56%) and p-naphthoquinone (77 mg, 97%) as an olive green solid m.p. 122°–125° which on recrystallisation from ethanol gave yellow needles (60 mg, 76%) m.p. 125°–126° (lit., 126) δ(CDCl$_3$) 8.27–7.67 (4H, m), and 7.00 (2H, S).

EXAMPLE 23

Oxidation of Hydroquinone

Hydroquinone (55 mg, 0.50 mmol) and bis-(p-methoxyphenyl)-telluroxide (196 mg, 0.55 mmol) were stirred in chloroform (2 ml) at room temperature under argon for 16 h. Separation of the reaction components by p.l.c. (benzene-ethyl acetate 9:1) gave bis-(p-methoxyphenyl)-telluride (8 mg, 4%) and p-benzoquinone (35 mg, 65%) as yellow needles m.p. 114°–115° (lit., 115.7°).

EXAMPLE 24

Oxidation of Phenylhydroxylamine

Phenylhydroxylamine (109 mg, 1 mmol) and bis-(p-methoxyphenyl)-telluroxide (376 mg, 1.05 mmol) were stirred in chloroform (4 ml) at room temperature under nitrogen for 0.1 h. Evaporation of the solvent and column chromatography (petroleum ether-ethyl acetate 9:1) gave bis-(p-methoxyphenyl)-telluride (150 mg, 88%) and nitrosobenzene (96 mg, 90%) m.p. 66°–68°).

EXAMPLE 25

Oxidation of p-Hydrazino benzoic acid p-Hydrazino benzoic acid (152 mg, 1 mmol) and bis-(p-methoxyphenyl)-telluroxide (394 mg, 1.10 mmol) were stirred in chloroform (10 ml) at room temperature for 24 h. The reaction mixture was then poured into saturated aqueous potassium carbonate, the phases separated and the aqueous phase extracted with dichloromethane (2×10 ml). The combined organic phases were dried over sodium sulphate and evaporated under reduced pressure. The residue after purification by column chromatography (chloroform) gave bis-(p-methoxyphenyl)-telluride (151 mg, 44%). The aqueous phase, on acidification with hydrochloric acid and extraction with dichloromethane gave a yellow solid (54 mg) which on sublimation under reduced pressure gave pure benzoic acid (32 mg, 26%) m.p. 122° (lit., 122°).

The following Examples 26–28 were performed at room temperature with 1.1 equivalents of bis-(p-methoxyphenyl)-telluroxide under nitrogen in dichloromethane, 2 ml of solvent being used for every 0.50 mmol of phenylhydrazine. Nitrogen was always evolved with 82% of the theoretical amount being measured in the oxidation of phenylhydrazine. The crude reaction mixtures were analysed by g.l.c. (2 m column, ⅛" o.d., 10% OV-17 on Chromosorb using a gradient temperature programme) for aromatic hydrocarbons and anisole. The amounts of aromatic hydrocarbons produced were estimated by comparing peak areas to those of standard solutions of benzene, toluene and m-xylene. The reaction mixtures were then subjected to p.l.c. to isolate the organo-tellurium products. The product yields together with reaction times and physical and spectroscopic data of the products are presented below.

EXAMPLE 26

Oxidation of Phenylhydrazine

Phenylhydrazine (121 mg, 1.12 mmol) was reacted with bis-(p-methoxyphenyl)-telluroxide for 0.2 h. to yield benzene (53%), p.l.c. (benzene-petroleum ether 2.8) afforded bis-(p-methoxyphenyl)-telluride (262 mg, 68%) and phenyl-p-methoxyphenyl-telluride (101 mg, 29%) m.p. 59°–62°. The latter on recrystallisation from methanol gave white needles, m.p. 61°–62° (lit., 60.5–61.5), δ(CDCl$_3$) 7.63 (d, J 8 Hz), 7.72–7.00 (m), 6.70 (d, j 8 Hz) combined integral 9H and 3.73 (3H, S), m/e 314(+), 184(100%) 169, 141 and 77 (Found: C, 50.03; H, 3.86 Calc. for C$_{13}$H$_{12}$O Te: C, 50.07; H, 3.88%).

EXAMPLE 27

Oxidation of p-Tolylhydrazine p-Tolylydrazine (61 mg, 0.50 mmol) was reacted with bis-(p-methoxyphenyl)-telluroxide for 0.2 h. to yield toluene (30%); p.l.c. (benzene-petroleum ether 1:1) afforded bis-(p-methoxyphenyl)-telluride (102 mg, 59%) and p-tolyl-p-methoxyphenyltelluride (28) (43 mg, 26%). The latter, on recrystallisation from methanol gave white needles, m.p. 65.5°–67° (lit., 64°–64.5°), δ(CDCl$_3$) 7.67 and 7.47 (both d, J 9 Hz, combined integral 4H), 6.93 and 6.70 (both d, J 9 Hz, combined integral 4H), 3.77 (3H,S), and 2.30 (3H, S), m/e 328 (M+), 210, 198 (100%), 183, 145, 91, 77 and 65 (Found: C, 51.62; H, 4.31 Calc. for C$_{14}$H$_{14}$O Te: C, 51.60; H 4.33%).

EXAMPLE 28

Oxidation of 2,6-Dimethylphenylhydrazine 2,6-Dimethylphenylhydrazine (68 mg, 0.50 mmol) was reacted with bis-(p-methoxyphenyl)-telluroxide for 0.2 h. to yield m-xylene (70%, p.l.c. (benzene-petroleum ether 1:1) afforded bis-(p-methoxyphenyl)-telluride (126 mg, 74%) and what appears to be 2,6-dimethylphenyl-4-methoxyphenyl-telluride as a colourless oil, m/e 342 (M+, 100%), 234, 212, 197, 105, 104, 79, 77, and 77.

EXAMPLE 29

Oxidation of Benzophenone Hydrazone

Benzophenone hydrazone (98 mg, 0.50 mmol) and bis-(p-methoxyphenyl)-telluroxide were stirred in chloroform (4 ml) under nitrogen for 22 h. p-Anisic acid (152 mg, 1 mmol) was then added to the deep red solution which was briefly heated to reflux temperature and then allowed to stir at room temperature for 1 h. The resulting pale yellow solution was washed with aqueous potassium carbonate, dried over magnesium sulphate and the solvent evaporated under reduced pressure. Column chromatography (benzene-petroleum ether 1:1) of the residue after conversion of the telluride into its dibromide afforded the benzhydryl ester of p-anisic acid (122 mg, 77%) m.p. 95°–96° (lit., 96°), m/e 318 (M+), 182, 167 (100%), 166, 165, 135, 105, 91, and 77.

EXAMPLE 30

Oxidation of 5α-Cholestan-3β-ol-selenobenzoate

The selenobenzoate:

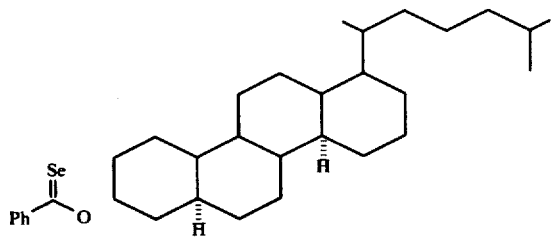

(139 mg, 0.25 mmol) and 4-methoxy-4'-dimethylaminodiphenyl-telluroxide (102 mg, 0.28 mmol) were stirred in chloroform (2 ml) at room temperature under nitrogen for 1 hr. The reaction mixture was concentrated by partial evaporation of the solvent, filtered to remove selenium (18 mg, 90%) and subjected to p.l.c. (petroleum ether-ethyl acetate 9:1) to afford 5α-cholestan-3β-ol-benzoate (120 mg, 97%) m.p. 135°–136° (lit., 136°–137°) and 4-methoxy-4'-dimethylaminodiphenyl-telluride (88 mg, 99%) m.p. 95°–96° (lit., 96°–97° which on recrystallisation from methanol gave fine white needles m.p. 97°–98°, δ(CDCl$_3$) 7.62 and 7.53 (combined integral 4H, both d, J 9 Hz), 6.68 and 6.53 (combined integral 4H, both d, J 9 Hz), 3.72 (3H, S), and 2.92 (6H, S), m/e 357 (M+), 250, 227, and 212 (100%) (Found: C, 50.95; H, 487; N, 3.78 Calc. for C$_{15}$H$_{17}$NOTe: C, 50.76; H, 4.83; N, 3.95%).

EXAMPLE 31

Oxidation of 5-Cholesten -3β-ol-thionobenzoate

5-Cholesten-3β-ol-thionobenzoate (230 mg, 0.45 mmol) and diphenyltelluroxide (150 mg, 0.50 mmol) were stirred in chloroform at room temperature under nitrogen for 2 h. The reaction mixture was then evaporated to dryness under vacuum and the components separated by column chromatography (petroleum ether followed by petroleum ether-ethyl acetate 20:1) to afford sulphur (14 mg, 97%), 5-cholesten-3β-ol-benzoate (202 mg, 92%) m.p. 144°–145° (lit., 150°–151°) and diphenyltelluride (115 mg, 91%) νmax (neat) 3064, 1575, 1475, 1435, 1017, 998, 726, 688, 660 and 640 cm$^{-1}$, δ(CDCl$_3$) 7.72 –7.47 and 7.25–7.02 (integral ratio 2:3, both m), m/e 284 (M+), 207, 154 (100%), 153, 77, and 51.

EXAMPLE 32

Oxidation of 5α-Cholestan-3β-ol-selenobenzoate using bis-(p-methoxycarbonylmethoxyphenyl) telluroxide The selenobenzoate (100 mg, 0.180 mmol) and the telluroxide (110 mg, 0.232 mmol) were stirred in chloroform (5 ml) at room temperature under nitrogen for 20 h. The reaction mixture was filtered to give selenium (13 mg, 92%) and column chromatography (petroleum ether-ethyl acetate 9:1) of the filtrate afforded 5α-cholestan-3β-ol-benzoate (76 mg, 85%) m.p. 135°–136° (lit., 136°–137° ) and bis-(p-methoxy-carbonylmethoxyphenyl) telluride (16 mg, 19%).

EXAMPLE 33

Oxidation of 5-Cholesten-3β-ol-thionobenzoate using symdibromo-tetrachloroethane, Bis-(p-methoxyphenyl)-telluride, Water and Triethylamine (a) Thionobenzoate: bis-(p-methoxyphenyl)-telluride 1:1 The thionobenzoate (100 mg, 0.198 mmol), symdibromo-tetrachloroethane (323 mg, 0.991 mmol), bis-(p-methoxyphenyl)-telluride (68 mg, 0.198 mmol), and triethylamine (136 μl, 1.0 mmol) were stirred together at room temperature in a two phase system of water (3 ml) and chloroform (2 ml). After 15 h. the phases were separated, the aqueous phase extracted with chloroform (2×5 ml) and the combined organic phases dried over sodium sulphate. Evaporation of the chloroform and column chromatography (petroleum ether followed by petroleum ether-ethyl acetate 20:1) of the residue gave 5-cholesten-3β-ol-benzoate (83 mg, 86%) m.p. 143°–145° (lit., 150°–151°). The i.r. spectrum was identical to that of an authentic sample.

(b) Thionobenzoate: Bis-(p-methoxyphenyl)-telluride 1:0.01

The thionobenzoate (100 mg, 0.198 mmol), sym-dibromo-tetrachloroethane (323 mg, 0.991 mmol), bis-(p-methoxyphenyl)telluride (0.6 mg, 0.0018 mmol), triethylamine (136 μl, 1.0 mmol) and water (36 μl, 2.0 mmol) were stirred together at room temperature in chloroform (2 ml). After 44 h. t.l.c. (petroleum ether followed by petroleum ether-ethyl acetate 20:1) showed the presence of both starting material and 5-cholesten-3β-ol-benzoate. Stirring at room temperature for a further 48 h. did not seem to improve the yield of product. The reaction mixture was subjected to p.l.c. (petroleum ether followed by petroleum ether-ethyl acetate 20:1) to afford 5-cholesten-3βol-benzoate (40 mg, 41%) and thionobenzoate (36 mg, 36%).

EXAMPLE 34

Catalytic Oxidation using 4-Methoxy-4'-dimethylaminodiphenyltellurium dichloride 5-Cholesten-3β-ol-thionobenzoate (100 mg, 0.198 mmol), symdibromo-tetrachloroethane (323 mg, 0.991 mmol), and 4-methoxy-4'-dimethylaminodiphenyltellurium dichloride (8.4 mg, 0.0198 mmole) were stirred in a two phase system of chloroform (2 ml) and aqueous potassium carbonate (2.5 ml, 20%) at room temperature for 4 h. T.l.c. (petroleum ether followed by petroleum ether-ethyl acetate 20:1) showed complete reaction. The two phases were separated, the aqueous phase extracted with chloroform (2×5 ml) and the combined chloroform extracts dried over magnesium sulphate. Filtration, evaporation of the solvent and column chromatography (petroleum ether followed by petroleum ether-ethyl acetate 20:1) of the residue afforded 5-cholesten-3β-ol-benzoate (85 mg, 88%) m.p. 143°–145° (lit; 150°–151°). The i.r. spectrum was identical to that of an authentic sample.

EXAMPLE 35

Catalytic Oxidation using 4-Methoxy-4'-dimethylaminodiphenyltelluride

5-Cholesten-3β-ol-thionobenzoate (100 mg, 0.198 mmol), symdibromo-tetrachloroethane (323 mg, 0.991 mmol, and 4-methoxy-4'-dimethylaminodiphenyltelluride (0.7 mg, 0.00198 mmol) were stirred in a two phase system of chloroform (2 ml) and aqueous potassium carbonate (2.5 ml, 20%) at room temperature for 47 h. The reaction was worked up in exactly the same way as described above to afford 5-cholesten-3β-ol-benzoate (75 mg, 77%) m.p. 144°–145° (lit., 150°–151°). The i.r. spectrum was identical to that of an authentic sample.

EXAMPLE 36

Oxidation of 5-Cholesten-3β-ol-thionobenzoate

Tetramethylenetellurium diiodide was prepared according to the method of Morgan G. T. and Burstall F. H., J. Chem. Soc. 1931, 180. The thionobenzoate (100 mg, 0.198 mmol), symdibromotetrachloroethane (323 mg, 0.991 mmole) and tetramethylenetellurium diiodide (8.6 mg. 0.0198 mmol) were stirred in a two phase system of chloroform (2 ml) and aqueous potassium carbonate (2.5 ml, 20%) at room temperature for 19 h. Analysis of the reaction mixture by t.l.c. (petroleum ether followed by petroleum ether-ethyl acetate 20:1) revealed the absence of any oxo-derivative. A further portion of tetramethylenetellurium diiodide (86 mg, 0.197 mmol) was added and stirring was continued for a total of 144 h. The two phases were separated, the aqueous phase extracted with chloroform (2×5 ml) and the combined chloroform extracts dried over magnesium sulphate. Filtration, evaporation of the solvent and column chromatography (petroleum ether followed by petroleum ether-ethyl acetate 20:1) of the residue afforded 5-cholesten-3β-ol-benzoate (56 mg, 58%). The i.r. spectrum was identical to that of an authentic sample.

We claim:

1. A process for the preparation of a compound of formula:

$$R^3(X^1)_mCO(X^2)_nR^4$$

wherein $X^1$ and $X^2$ which may be the same or different, each represents an oxygen or sulphur atom or the group —NH—; m and n, which may be the same or different are each 0 or 1; and $R^3$ and $R^4$, which may be the same or different, each represents a hydrogen atom, a $C_{1-5}$ alkyl or alkenyl group, a $C_{1-32}$ cycloalkyl group optionally including double bonds, a $C_{7-10}$ aralkyl group or a $C_{6-12}$ aryl group such groups optionally being substituted by halogen, amino, carboxyl, hydroxy, $C_{1-6}$ alkyl and/or $C_{1-6}$ alkoxy; or $R^3$ and $R^4$ together form a ring(s) which may possess up to 32 carbon atoms and which may have double bonds and be optionally substituted by halogen, amino, carboxyl, hydroxy, $C_{1-6}$ alkyl and/or $C_{1-6}$ alkoxy which process comprises oxidising a compound of formula:

$$R^3(X^1)_mCY(X^2)_nR^4$$

wherein Y represents a sulphur or selenium atom; and $X^1$, $X^2$, $R^3$, $R^4$, m and n are as herein defined by means of a telluroxide of the formula:

$$R-\underset{\underset{O}{\|}}{Te}-R^1$$

wherein R and $R^1$, which may be the same or different each represent a phenyl group optionally substituted by halogen, $C_{1-6}$ alkyl, phenyl, phenoxy, di($C_{1-6}$alkyl) amino, hydroxy, carboxy, chlorocarbonyl, nitro and/or $C_{1-6}$ alkoxy optionally substituted by an alkoxycarbonyl group in which the alkoxy moiety contains 1 to 6 carbon atoms; or R and $R^1$ together with the tellurium atom therebetween represent a group selected from

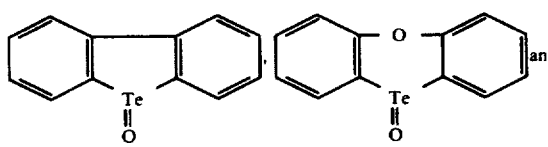 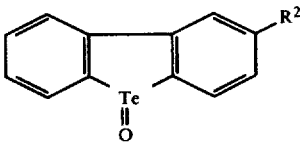

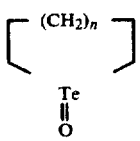

in which n is 0 or 1, which group may optionally be substituted by halogen, $C_{1-6}$ alkyl, phenyl, phenoxy, di($C_{1-6}$alkyl) amino, hydroxy, carboxy, chlorocarbonyl, nitro or $C_{1-6}$ alkoxy optionally substituted by an alkoxycarbonyl group in which the alkoxy moiety contains 1 to 6 carbon atoms.

2. A process as claimed in claim 1 wherein the telluroxide is a compound of formula:

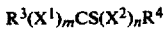

$$R\text{—}Te\text{—}R^1 \quad (I)$$
$$\|$$
$$O$$

in which R and $R^1$, which may be the same or different, each represents an optionally substituted aryl or heterocyclic group or R and $R^1$ together with the tellurium atom therebetween represent a heterocyclic ring, which may contain one or more further heteroatoms and which may carry substituents and/or fused aromatic rings.

3. A process as claimed in claim 2 wherein the telluroxide is a compound of formula:

in which $R^2$ represents a hydrogen atom, a methyl group or an electron donating substituent.

4. A process as claimed in claims 2, 3 or 1 wherein a compound of formula $$R^3(X^1)_mCS(X^2)_nR^4 \quad (VI)$$

wherein $X^1$ and $X^2$, which may be the same of different, each represents a sulphur, oxygen or the grove NH; m and n, which may be the same or different, are each 0 or 1; and $R^3$ and $R^4$, which may be the same or different, each represents a hydrocarbyl group or together they form one or more rings which may possess up to 32 carbon atoms and optionally contain one or more double bonds and/or optionally carry one or more substituent is oxidised to a compound of formula:

$$R^3(X^1)_mCO(X^2)_nR^4 \quad (VII)$$

in which $R^3$, $R^4$, $X^1$, $X^2$, m and n are as defined above.

5. A process as claimed in claim 1 in which the telluroxide is prepared in situ by reaction of the corresponding telluride in the presence of water and a base with a halogenating agent capable of halogenating tellurides.

6. A process as claimed in claim 5 in which the telluride is present initially and an excess of halogenating agent serves continually to regenerate the telluroxide under the conditions of the reagent system.

7. The process of claim 4 wherein m and n are 1.

8. The process of claim 7 wherein the compound of formula (VI) is 1,3-diphenylthiourea.

* * * * *